US010610191B2

(12) United States Patent
Sjolin et al.

(10) Patent No.: US 10,610,191 B2
(45) Date of Patent: Apr. 7, 2020

(54) MANAGING GEOMETRIC MISALIGNMENT IN X-RAY IMAGING SYSTEMS

(71) Applicant: Prismatic Sensors AB, Stockholm (SE)

(72) Inventors: Martin Sjolin, Stockholm (SE); Xuejin Liu, Taby (SE); Mats Danielsson, Taby (SE)

(73) Assignee: PRISMATIC SENSORS AB, Stockholm (SE)

( * ) Notice: Subject to any disclaimer, the term of this patent is extended or adjusted under 35 U.S.C. 154(b) by 247 days.

(21) Appl. No.: 15/642,754

(22) Filed: Jul. 6, 2017

(65) Prior Publication Data

US 2019/0008474 A1 Jan. 10, 2019

(51) Int. Cl.
*A61B 6/00* (2006.01)
*A61B 6/06* (2006.01)
*A61B 6/03* (2006.01)

(52) U.S. Cl.
CPC ............... *A61B 6/587* (2013.01); *A61B 6/06* (2013.01); *A61B 6/4233* (2013.01); *A61B 6/4241* (2013.01); *A61B 6/4291* (2013.01); *A61B 6/585* (2013.01); *A61B 6/586* (2013.01); *A61B 6/032* (2013.01); *A61B 6/5252* (2013.01); *A61B 6/5258* (2013.01)

(58) Field of Classification Search
CPC ....... A61B 6/587; A61B 6/4291; A61B 6/586; A61B 6/585; A61B 6/4233; A61B 6/4241; A61B 6/06; A61B 6/5258; A61B 6/5252; A61B 6/032
See application file for complete search history.

(56) References Cited

U.S. PATENT DOCUMENTS

| 4,429,227 A | 1/1984 | Dibianca et al. |
| 4,731,534 A | 3/1988 | Klein et al. |
| 5,144,141 A | 9/1992 | Rougeot et al. |
| (Continued) | | |

FOREIGN PATENT DOCUMENTS

EP 1 408 347 A1 4/2004

OTHER PUBLICATIONS

Written Opinion issued in Application No. PCT/SE2018/050660, dated Sep. 7, 2018.
(Continued)

*Primary Examiner* — Christine S. Kim
(74) *Attorney, Agent, or Firm* — Young & Thompson

(57) ABSTRACT

Disclosed is a method for management of geometric misalignment in an x-ray imaging system having an x-ray source, a photon-counting x-ray detector and an intermediate collimator structure in the x-ray path between the x-ray source and the x-ray detector. The x-ray detector includes a plurality of pixels, and the collimator structure includes a plurality of collimator cells, wherein each of at least a subset of the collimator cells corresponds to a N×M matrix of pixels, where at least one of N and M is greater than one. The method includes monitoring, for a designated subset of pixels including at least two pixels that are affected differently by shadowing from the collimator structure due to geometric misalignment, output signals from the pixels of the designated subset, and determining the occurrence of geometric misalignment based on the monitored output signals from the pixels of the designated subset of pixels.

24 Claims, 21 Drawing Sheets

(56) References Cited

U.S. PATENT DOCUMENTS

| | | | |
|---|---|---|---|
| 5,373,162 | A | 12/1994 | Akai |
| 5,378,894 | A | 1/1995 | Akai |
| 6,266,434 | B1 | 7/2001 | Toth et al. |
| 2004/0251420 | A1 | 12/2004 | Sun |
| 2007/0029495 | A1* | 2/2007 | Petrillo ............. H01L 27/14658 |
| | | | 250/370.14 |
| 2010/0204942 | A1 | 8/2010 | Danielsson et al. |
| 2012/0232385 | A1 | 9/2012 | Hattori et al. |
| 2015/0049857 | A1* | 2/2015 | Wiednnann .......... G01N 23/046 |
| | | | 378/19 |
| 2015/0324973 | A1 | 11/2015 | Ueki et al. |
| 2016/0199019 | A1* | 7/2016 | Ruimi .................... A61B 6/032 |
| | | | 378/9 |
| 2018/0177481 | A1* | 6/2018 | Jacob ................... A61B 6/4241 |
| 2018/0317869 | A1* | 11/2018 | Rui ...................... A61B 6/4291 |

OTHER PUBLICATIONS

International Search Report issued in Application No. PCT/SE2018/050660, dated Sep. 7, 2018.

Atsuro Suzuki, et al., A four-pixel matched collimator for high-sensitivity SPECT imaging, Physics in Medicine and Biology, 2013, pp. 2199-2217, vol. 58, IOP Publishing.

Robert E. Alvarez, Estimator for photon counting energy selective x-ray imaging with multibin pulse height analysis, Medical Physics, May 2011, pp. 2324-2334, vol. 38, No. 5.

\* cited by examiner

MANAGING GEOMETRIC MISALIGNMENT IN X-RAY IMAGING SYSTEMS

TECHNICAL FIELD

The present invention relates generally to the technical field of x-ray imaging, and more particularly to a method and system for management of geometric misalignment in an x-ray imaging system, a corresponding x-ray imaging system and a corresponding computer-program product.

BACKGROUND

Radiographic imaging such as x-ray imaging has been used for years in medical applications and for non-destructive testing.

Normally, an x-ray imaging system includes an x-ray source and an x-ray detector system. The x-ray source emits x-rays that pass through a subject or object to be imaged and are then registered by the x-ray detector system. Since some materials absorb a larger fraction of the x-rays than others, an image is formed of the subject or object.

It may be useful to begin with a brief overview of an illustrative overall x-ray imaging system, with reference to FIG. 1. In this non-limiting example, the x-ray imaging system 100 basically comprises an x-ray source 10, an x-ray detector system 20 and an associated image processing device 30. In general, the x-ray detector system 20 is configured for registering radiation from the x-ray source 10 that may have been focused by optional x-ray optics and passed an object or subject or part thereof. The x-ray detector system 20 is connectable to the image processing device 30 via suitable analog processing and read-out electronics (which may be integrated in the x-ray detector system 20) to enable image processing and/or image reconstruction by the image processing device 30.

As illustrated in FIG. 2, another example of an x-ray imaging system 100 comprises an x-ray source 10, which emits x-rays; an x-ray detector system 20, which detects the x-rays after they have passed through the object; analog processing circuitry 25, which processes the raw electrical signal from the detector and digitizes it; digital processing circuitry 40 which may carry out further processing operations on the measured data such as applying corrections, storing it temporarily, or filtering; and a computer 50 which stores the processed data and may perform further post-processing and/or image reconstruction.

The overall detector may be regarded as the x-ray detector system 20, or the x-ray detector system 20 combined with the associated analog processing circuitry 25.

The digital part including the digital processing circuitry 40 and/or the computer 50 may be regarded as a digital image processing system 30, which performs image reconstruction based on the image data from the x-ray detector. The image processing system 30 may thus be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used x-ray imaging system is a Computed Tomography (CT) system. FIG. 3 is a schematic diagram illustrating an example of a CT system. In the example of FIG. 3, the CT system may include an x-ray source that produces a fan- or cone-beam of x-rays and an opposing x-ray detector system for registering the fraction of x-rays that are transmitted through a patient or object. The x-ray source and detector system are normally mounted in a gantry that rotates around the imaged object. Accordingly, the x-ray source and the x-ray detector system illustrated in FIG. 3 may be arranged as part of a CT system, e.g. mountable in a CT gantry. The overall CT system may also include appropriate controllers and management systems.

FIG. 4 is a schematic diagram of an x-ray detector according to an exemplary embodiment. In this example there is shown a schematic view of an x-ray detector and x-ray source emitting x-rays. For example, the elements of the detector may be pointing back to the source, and they are preferably arranged in a slightly curved overall configuration. The dimensions and segmentation of the detector array affect the imaging capabilities of the x-ray imaging system. The direction of the incident x-rays is referred to as the y-direction. A plurality of detector pixels in the direction of the rotational axis of the gantry (referred as z-direction) enables multi-slice image acquisition. A plurality of detector pixels in the angular direction (referred as x-direction) enables measurement of multiple projections in the same plane simultaneously and this is applied in fan/cone-beam CT. Most conventional detectors have detector pixels in both the slice (z) and angular (x) directions.

Modern x-ray detectors normally convert the incident x-rays into electrons, typically through photo absorption and/or Compton interaction, and the resulting electrons create secondary visible light which in turn is detected by a photo-sensitive material. Other detectors are based on semiconductors that convert x-rays directly into electron-hole pairs that are collected by drifting the charge carriers in an applied electric field.

Most x-ray detectors used for medical imaging today are energy integrating, meaning the output signal is the sum of the energies of the photons that interacted during the measurement period. The contribution from each detected photon to the signal is thus proportional to the energy of the photon.

Photon-counting detectors have also emerged as a feasible alternative in some applications; currently photon-counting detectors are commercially available in, for example, mammography. Many photon-counting detectors are spectral (energy resolving), meaning that they can categorize detected photons based on the energy that is deposited in the detector material when the photon interacts. The energy categorization is performed using energy bins that are defined by programmable energy thresholds. The energy information can be used to obtain additional information about the composition of the object through which the photons have traversed. This additional information can in turn be used to increase the image quality and/or to decrease the radiation dose.

Compared to energy-integrating x-ray detector systems, photon-counting x-ray detector systems have the following advantages: the energy thresholds can be used to remove electronic noise that for energy-integrating detectors is included in the measured signal; the energy information can be used to perform so-called material basis decomposition, by which different materials and/or components in the examined subject can be identified and quantified (R. E. Alvarez, Medical Physics 38(5). 2324-2334, 2011); the detector has no afterglow (the detector produces signal output for a short time after the input signal has stopped) which increases the angular resolution; also, higher spatial resolution can be achieved by having a smaller pixel size. Materials for photon-counting x-ray detectors include cadmium telluride (CdTe), cadmium zinc telluride (CZT) and silicon (Si).

U.S. Pat. No. 8,183,535 discloses an example of a photon-counting edge-on x-ray detector. In this patent, there are multiple semiconductor detector modules arranged together to form an overall detector area, where each semiconductor detector module comprises an x-ray sensor oriented edge-on to incoming x-rays and connected to integrated circuitry for registration of x-rays interacting in the x-ray sensor.

The semiconductor detector modules are normally tiled together to form a full detector of almost arbitrary size with almost perfect geometrical efficiency.

FIG. 5 is a schematic diagram illustrating an example of a semiconductor detector module. This is an example of a semiconductor detector module with the sensor part split into detector elements, where each detector element is normally based on a diode having a charge collecting electrode as a key component. In the example of FIG. 5, the semiconductor sensor part is also split into so-called depth segments in the depth direction, assuming the x-rays enter through the edge.

Normally, a detector element is an individual x-ray sensitive sub-element of the detector. In general, the photon interaction takes place in a detector element and the thus generated charge is collected by the corresponding electrode of the detector element.

Depending on the detector topology, a detector element may correspond to a pixel, especially when the detector is a flat-panel detector. However, a depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode. The detector strips of a depth-segmented detector normally correspond to the pixels of an ordinary flat-panel detector.

The data output from a photon-counting spectral detector generally comprises the number of photons detected within an energy bin (pulse-heights between two thresholds), or the number of photons detected above an energy threshold. The photon-count data can be used to estimate the material compositions of the imaged object, a process commonly referred to as basis material decomposition. This can be done either in projection domain: the material thicknesses are estimated for each pixel individually and an image is formed for each basis material; or in the image domain: an image is formed for each energy bin, and the material estimation is performed using the different bin images.

Object collimators, also referred to as scatter rejection grids or anti-scatter grids, are commonly used in modern CT systems. Typically, they are embodied both in the angular (x) and the slice (z) directions with stacks of lamellas made by heavy metals, e.g., tungsten or molybdenum, to form walls of collimator cells, as illustrated in FIG. 6.

These collimator cells commonly hold a cell-to-pixel relationship to the detector pixels below for a better suppression of scattered radiation, as illustrated in FIG. 7. Reference can be made, e.g. to U.S. Pat. No. 9,583,228 B2, U.S. Pat. No. 8,831,181 B2, U.S. Pat. No. 7,362,849 B2. Aligning the collimator lamellas to the focus of the x-ray source in both x and z directions is a challenge, especially for densely packed detector pixels, e.g. referring to US 2013/0168567 A1.

Misalignment of the detector, the anti-scatter grid and the source leads to: errors in the geometric parameters of the image acquisition (the position at which each measurement is performed); and shadowing of the detector, which in turn can lead to loss of photons and changes of the spectral response of the detector.

Many methods have been developed for geometric calibration, i.e. estimation of the geometric parameters of the image acquisition, of CT imaging systems:

US 2014/0211925, U.S. Pat. No. 8,622,615 and US 2014/0153694 relate to geometric calibration for flat-panel detectors using a calibration phantom or device. The devices are not an integral part of the detector but placed in between the source and the detector.

U.S. Pat. No. 6,370,218, describes an invention in which the penumbra (partially illuminated region) of the x-ray illumination field is measured using a multi-slice x-ray detector to determine the position of the x-ray tube focal spot.

WO 2010/093314 mentions obtaining measurement information from an edge-on x-ray detector having depth segments and measuring the degree of shadowing using the ratio of the number of detected x-ray counts in the different depth segments.

U.S. Pat. No. 5,131,021 relates to an invention where a set of x-ray attenuating masks are placed on pixels outside of the imaged object. The position of the x-ray source in the axial (z) direction is then estimated based on ratios of the measured signal in pixels with different masks.

U.S. Pat. No. 8,262,128, a method is described for determining the location of the focal spot by having a set of anti-scatter lamella pointing towards a point other than the source location. The deliberately misaligned anti-scatter lamella cause shadowing on the detector pixels located next to the lamella and a movement of the source leads to a change of measured x-ray intensity which then can be used to estimate the source location.

Multi-pixel matched collimators (the collimator cells are matched to several detector pixels) has been suggested for single photon emission computed tomography (SPECT) system to achieve better detection efficiency. Reference can be made, e.g. to WO 2016162962 A1, WO 2011093127 A1, and A. Suzuki, et al., Physics in Medicine and Biology 58.7 (2013): 2199th. However, multi-pixel matched collimators are generally not used for CT. An example of a multi-pixel matched collimator is illustrated in FIG. 12.

There are three types of misalignments that can lead to shadowing of the detector (i.e., part of the detector cannot be illuminated by x rays) from the object collimator. The first type is misalignment of the x-ray source (either in x- or z-direction) in which case collimator lamellas will be in the path of incident x-ray beams and lead to different active cross-sections along the detector depth, as illustrated in FIG. 8. The second type is misalignment of the detector (either in x- or z-direction), which will lead to the same situation as for misalignment of the x-ray source, as illustrated in FIG. 9. The third type is misalignment of the collimator lamella, which will always result in a fixed amount of inactive detector area along the detector depth, as illustrated in FIG. 10.

Shadowing from either misalignment of the source or the collimator, leads to loss of counts in shadowed pixels. Shadowing caused by source misalignment also results in different active cross-sections of detector material at different depths in the detector. Since the detector has different spectral response at different depths, this implies that the spectral response of each detector pixel will depend on the degree of shadowing. This effect will here be referred to as the non-linear spectral effect. Different spectral response results in a difficult normalization problem; the relative gain of each pixel (the output signal as a function of input signal) depends on the shape of the incoming x-ray spectrum. It is therefore difficult to remove pixel differences by, for example, normalizing the output signal by a single correction factor determined from a single reference measurement, e.g. an air scan (so called flat-fielding). If pixels with different spectral responses are left uncorrected, there is a risk that the reconstructed images have ring artifacts (rings of brighter or darker values due to higher or lower gain of a detector pixel compared its neighboring pixels).

Energy integrating detectors cannot correct for the different spectral responses even if the degree of shadowing in pixels can be properly known since there is no spectral information available. The pixels on an energy integrating detector must therefore have close to identical spectral response to cope with the non-linear spectral effect. This can, for example, be obtained by blocking the regions that risk shadowing (i.e. the edges of the pixel) with a highly attenuating material (illustrated in FIG. 11), referring to US 2016/0025867 A1, US 2013/0121475 A1, or by tilting collimator lamellas with respect to the detector array with a predetermined angle (could be more than 1° C.), referring to US 2013/0121475 A1, or by adjusting the heights of collimator lamellas to guarantee that the shadowing effect is smaller than a threshold (e.g., 5% reduction of detection efficiency), referring to CN 1596829 A.

For photon-counting spectral detectors, on the other hand, it is not necessary to have identical spectral response if images are formed using material basis decomposition in the projection domain. Any spectral differences that are the same during system calibration as during image acquisition scans (e.g. static misalignments) can be removed by performing material basis decomposition with a forward model [6] that accurately captures pixel-dependent detector responses. The forward model can for example be obtained from a material calibration during the system calibration (R. E. Alvarez, Medical Physics 38(5). 2324-2334, 2011).

However, for dynamic misalignment, caused by e.g. mechanical movements during scans, there is no prior knowledge from the system calibration and therefore it cannot be corrected with calibration data. Although a source monitor can be used to monitor the position of the x-ray source for further correction, it is difficult to achieve a high degree of accuracy. For energy-integrating detectors, the effects of dynamic misalignment are mitigated using, for example, the method suggested in US 2016/0025867 A1, which requires an extra grid between the object collimator and the detector to provide more shielding and thus guarantee uniform active area among different detector pixels also if for example the source has moved during a scan.

An illustration is shown in FIG. 11 where pixel A and pixel B have the same active area even though there are misalignments both of collimator lamella and the source. However, the method implies a big sacrifice of geometric efficiency of the detector, which can be seen from FIG. 11 (the x-rays that are blocked by the extra grid are lost), and this sacrifice will be larger if the method is used for photon-counting detectors due to their smaller pixel sizes.

SUMMARY OF THE INVENTION

It is a general object to improve the performance of x-ray imaging systems such as CT systems.

It is a specific object to provide a method for management of geometric misalignment in an x-ray imaging system.

It is also an object to provide a system configured for management of geometric misalignment in an x-ray imaging system.

Another object is to provide an x-ray imaging system comprising such a system. Yet another object is to provide a corresponding computer-program product. These and other objects are met by embodiments of the present invention.

According to a first aspect, there is provided a method for management of geometric misalignment in an x-ray imaging system having an x-ray source, a photon-counting x-ray detector and an intermediate collimator structure in the x-ray path between the x-ray source and the x-ray detector. The x-ray detector comprises a plurality of pixels, and the collimator structure comprises a plurality of collimator cells, wherein each of at least a subset of the collimator cells corresponds to a N×M matrix of pixels, where at least one of N and M is greater than one. The method comprises:

monitoring, for a designated subset of pixels including at least two pixels that are affected differently by shadowing from the collimator structure due to geometric misalignment, output signals from the pixels of the designated subset of pixels; and determining the occurrence of geometric misalignment based on the monitored output signals from the pixels of the designated subset of pixels.

In this way, geometric misalignment in an x-ray imaging system can be efficiently handled.

According to a second aspect, there is provided a system configured for management of geometric misalignment in an x-ray imaging system having an x-ray source, a photon-counting x-ray detector and an intermediate collimator structure in the x-ray path between the x-ray source and the x-ray detector. The x-ray detector comprises a plurality of pixels, and the collimator structure comprises a plurality of collimator cells, wherein each of at least a subset of the collimator cells corresponds to a N×M matrix of pixels, where at least one of N and M is greater than one. The system is configured to monitor, for a designated subset of pixels including at least two pixels that are affected differently by shadowing from the collimator structure due to geometric misalignment, output signals from the pixels of the designated subset of pixels. The system is configured to determine the occurrence of geometric misalignment based on the monitored output signals from the pixels of the designated subset of pixels.

According to a third aspect, there is provided an x-ray imaging system comprising such a system.

According to a fourth aspect, there is provided a computer-program product comprising a computer-readable medium having stored thereon a computer program for management, when executed by a processor, of geometric misalignment in an x-ray imaging system having an x-ray source, a photon-counting x-ray detector and an intermediate collimator structure in the x-ray path between the x-ray source and the x-ray detector. In this application, the x-ray detector comprises a plurality of pixels, and the collimator structure comprises a plurality of collimator cells, wherein each of at least a subset of the collimator cells corresponds to a N×M matrix of pixels, where at least one of N and M is greater than one. The computer program comprises instructions, which when executed by the processor, cause the processor to:

monitor, for a designated subset of pixels including at least two pixels that are affected differently by shadowing from the collimator structure due to geometric misalignment, output signals from the pixels of the designated subset of pixels; and determine the occurrence of geometric misalignment based on the monitored output signals from the pixels of the designated subset of pixels.

According to a fifth aspect, there is provided an x-ray detector comprising:

a plurality of edge-on detector modules arranged side-by-side and adapted to be oriented edge-on towards an x-ray source, each edge-on detector having at least one detector pixel; and a collimator structure arranged in the x-ray path between the x-ray source and the edge-on detector modules, wherein the collimator structure comprises at least one collimator cell corresponding to an N×M matrix of pixels, where at least one of N and M is greater than one, and at least one collimator lamella of the collimator cell is arranged to be offset relative a boundary between pixels.

According to a sixth aspect, there is provided an x-ray detector comprising:

a plurality of edge-on detector modules arranged side-by-side and adapted to be oriented edge-on towards an x-ray source;

an x-ray attenuating structure arranged between at least a subset of the edge-on detector modules; and a collimator structure arranged in the x-ray path between the x-ray source and the edge-on detector modules, wherein the collimator structure comprises at least one collimator lamella arranged as an extension of the x-ray attenuating structure and having a larger thickness than the thickness of the x-ray attenuating structure situated between the edge-on detector modules.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION OF THE INVENTION

Figure 18:
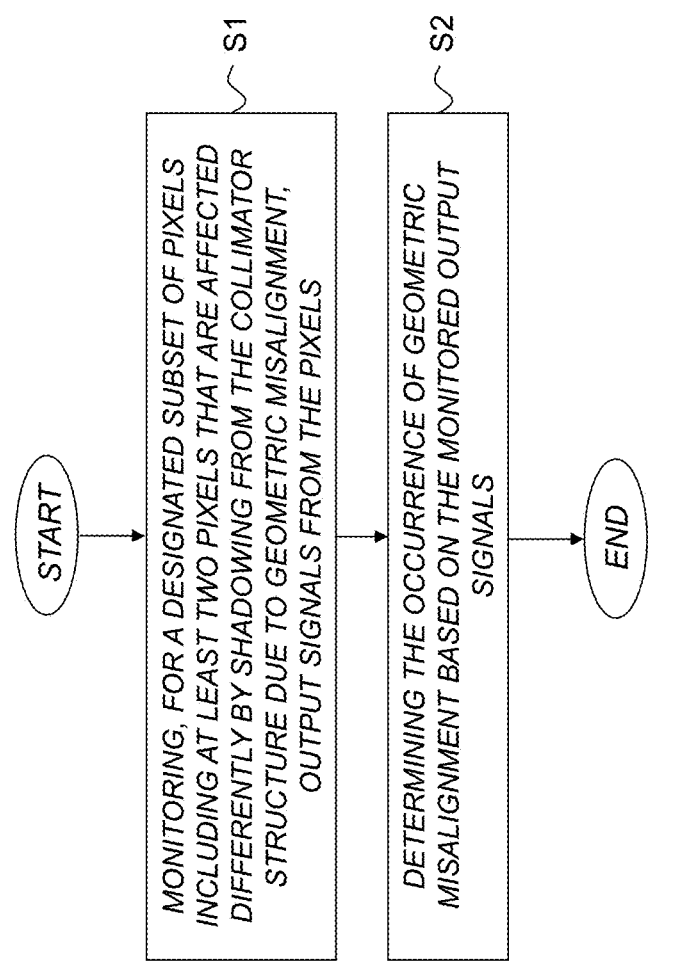
FIG. 18 is a schematic flow diagram illustrating an example of a method for management of geometric misalignment in an x-ray imaging system

FIG. 18 is a schematic flow diagram illustrating an example of a method for management of geometric misalignment in an x-ray imaging system having an x-ray source, a photon-counting x-ray detector and an intermediate collimator structure in the x-ray path between the x-ray source and the x-ray detector.

In general, the x-ray detector comprises a plurality of pixels, and the collimator structure comprises a plurality of collimator cells, wherein each of at least a subset of the collimator cells corresponds to a N×M matrix of pixels, where at least one of N and M is greater than one.

In a particular example, N≥2 and M≥2.

Basically, the method comprises:

S1: monitoring, for a designated subset of pixels including at least two pixels that are affected differently by shadowing from the collimator structure due to geometric misalignment, output signals from the pixels of the designated subset of pixels; and S2: determining the occurrence of geometric misalignment based on the monitored output signals from the pixels of the designated subset of pixels.

For example, the at least two pixels have different responses to the shadowing, and the different responses are monitored by measuring the output signals.

By way of example, the method further comprises i) estimating at least one parameter representing the geometric misalignment and/or ii) correcting for the geometric misalignment based on the monitored output signals from the pixels of the designated subset of pixels and/or iii) performing post-processing of the output signals and/or iv) image reconstruction based on the parameter(s) representing the geometric misalignment and/or based on the monitored output signals from the pixels of the designated subset of pixels.

In a particular example, the effect of the geometric misalignment on the output signal(s), or on value(s) based on the output signal(s), of at least one pixel is corrected for based on the monitored output signals from the pixels of the designated subset of pixels.

For example, the at least one pixel to be corrected for is located behind the object/subject to be imaged during image acquisition.

Preferably, the output signals from the pixels represent photon counts of the pixels.

In a particular example the output signals from the pixels of the designated subset of pixels are measured during image acquisition of an object/subject and located outside of the object/subject to be imaged during measurement.

For example, the at least two pixels that are affected differently by shadowing are located with respect to the collimator structure such that they experience different shadowing from the collimator structure due to geometric misalignment.

As an example, said at least two pixels that are affected differently by shadowing may include a first subset of one or more pixels having an increase in the number of photon counts as a consequence of the shadowing and a second subset of one or more pixels having a decrease in the number of photon counts as a consequence of the shadowing.

In a particular example, each of the collimator cells has a first side and a second opposite side, and at least one of the pixels of the designated subset is located on the first side of a collimator cell and at least one of the pixels of the designated subset is located on the second opposite side of the same or another collimator cell.

For example, the x-ray detector comprises a number of detector modules, and the pixels located on opposite sides of a collimator cell belong to different detector modules of the x-ray detector.

In a typical example, the geometric misalignment may include a relative geometric misalignment between the x-ray source and the x-ray detector.

As an example, the direction and/or degree of pixel shadowing caused by the geometric misalignment may be determined based on the monitored output signals from the pixels of the designated subset of pixels.

In a particular embodiment, the x-ray detector is a photon-counting and energy-discriminating x-ray detector, and the effect of the geometric misalignment on the photon count(s) of said at least one pixel is corrected for based on the monitored output signals, or on value(s) based on the output signal(s), of the pixels of the designated subset of pixels and the associated photon energy information obtained from the photon-counting and energy-discriminating x-ray detector.

For example, the photon-counting and energy-discriminating x-ray detector may be configured to classify the detected photons into energy bins, and the step of correcting for the effect of the geometric misalignment on the photon count(s) may comprise applying correction to the photon count(s) in the energy bins of the said at least one pixel based on the monitored photon counts of the pixels of the designated subset of pixels and the associated photon energy information.

Optionally, correction factors may be determined based on at least one parameter representing the geometric misalignment and basis material thickness.

As an example, the correction factors may be determined and applied for the photon counts in lower energy bins.

In another example, a geometric misalignment may be distinguished from a drop in current-to-peak-kilovoltage ratio (mA/kVp) of the x-ray source based on the monitored output signals of the pixels of the designated subset of pixels.

Generally, the management of geometric misalignment may include, e.g. supervision and/or handling of the geometric misalignment such as monitoring and/or correcting/calibrating for the geometric misalignment.

For a better understanding, the technology will now be described with reference to non-limiting examples.

In some aspect(s), there is provided a method and corresponding embodiments for the geometrical calibration of a photon-counting x-ray detector system with energy discrimination ability. In a particular embodiment, the method is based on having several detector pixels within a collimator cell, monitoring the variations in the measured counts in pixels outside of the imaged object and using this information to correct the measurements that are performed by pixels located behind the imaged object.

In the same or other aspect(s), the invention relates to management of the effects of geometric misalignment of the x-ray tube and the x-ray detector, and includes methods for: 1) estimating the relative geometric alignment between x-ray tube and detector based on measurements acquired by pixels on a photon-counting and spectral detector located outside of the imaged object, and 2) methods for correcting the output signal from detector pixels located behind the imaged object based on an estimation of the relative geometric alignment between the x-ray tube and the detector.

With reference to the figures, x, y, z-directions are defined as in a common CT system where x-direction is the gantry rotation direction, y-direction is the x-ray beam direction and z-direction is the slice direction (system axis).

The errors in the signal output from a detector pixel, e.g. photon counts, can come from dynamic changes of the un-attenuated x-ray beam quality or the response function of the detector pixels. The response function of a detector pixel is here defined as the output signal for a given input signal, e.g. the average number of registered counts in each energy bin when the pixel is illuminated with N photons of a certain energy.

The sources of the changes of the un-attenuated x-ray beam quality include, but are not limited to: drift of x-ray tube current (mA) and drift of x-ray tube acceleration voltage (kVp). Sources of change of the detectors response function include, but are not limited to, drift of the energy thresholds and change of the relative geometric alignment of the x-ray tube and the detector. If the signal output from pixels behind the object are not corrected for changes of the quality of the un-attenuated x-ray beam and/or changes of the response function of the detector pixels, the reconstructed images can contain artifacts, such as streaks or rings.

During a CT image acquisition, the measured signal in pixels that are located behind the imaged object naturally change over time due to the relative rotation of the object and the detector/source. This implies that fluctuations in the measured counts due to changes of the detector response function are difficult to detect. However, many misalignments, such as movement of the x-ray tube focal spot or movement of the detector, affect the entire detector at the same time. This implies that detector pixels that are located outside of the imaged object can be used to monitor movements of the source relative to the detector as long as the pixels located outside of the imaged object are sensitive to misalignment.

In the disclosed invention, sensitivity to misalignment is achieved by having multiple pixels located inside each collimator cell. In other words, the collimator structure comprises a plurality of collimator cells, wherein each of at least a subset of the collimator cells corresponds to a N×M matrix of pixels, where at least one of N and M is greater than one. This type of collimator is sometimes referred to as a multi-pixel matched collimator.

In a particularly practical example, N≥2 and M≥2.

Figure 1:
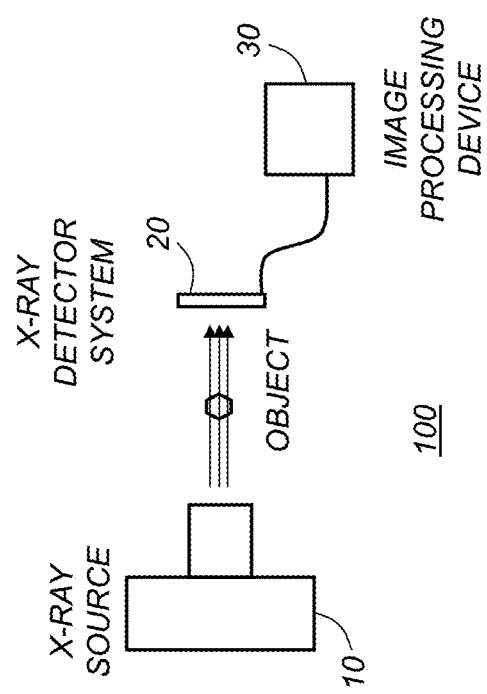
FIG. 1 is a schematic diagram illustrating an example of an overall x-ray imaging system.
Figure 2:
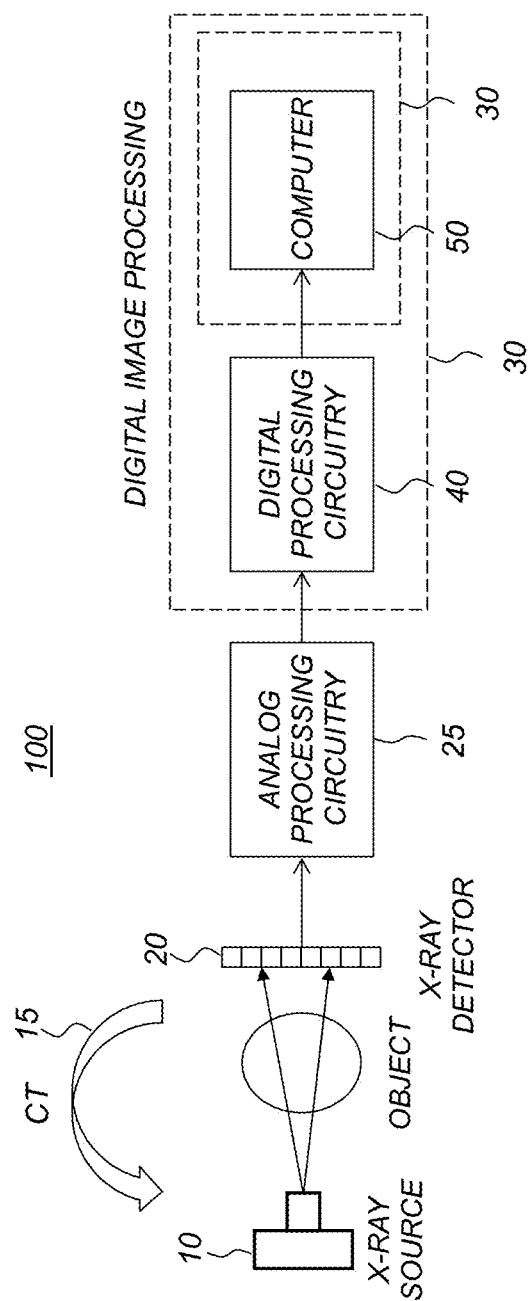
FIG. 2 is a schematic diagram illustrating another example of an x-ray imaging system.
Figure 3:
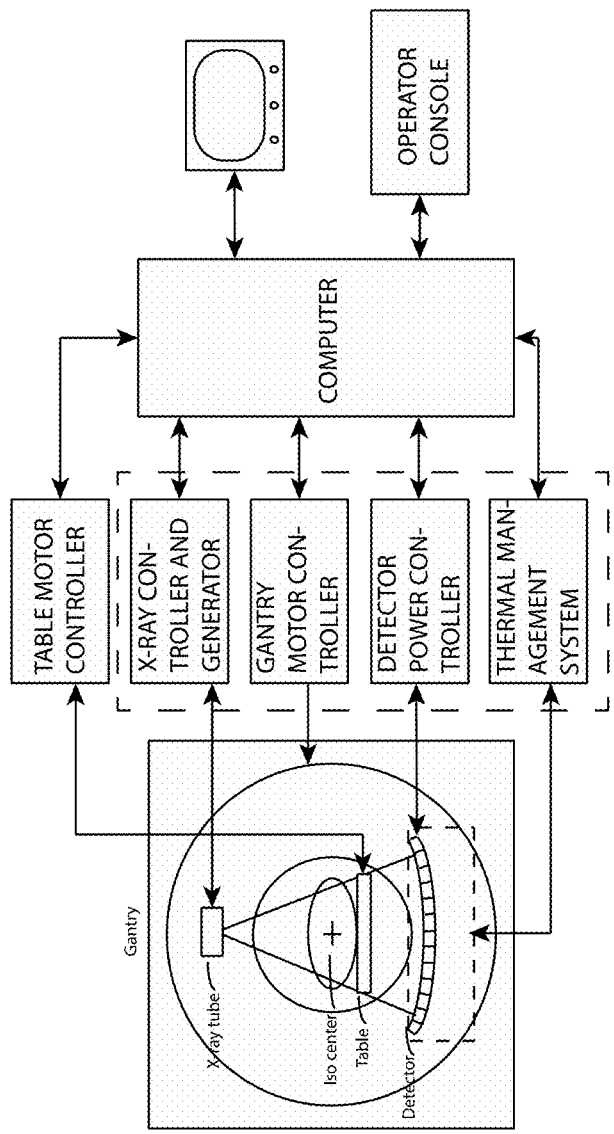
FIG. 3 is a schematic diagram illustrating an example of a CT system.
Figure 4:
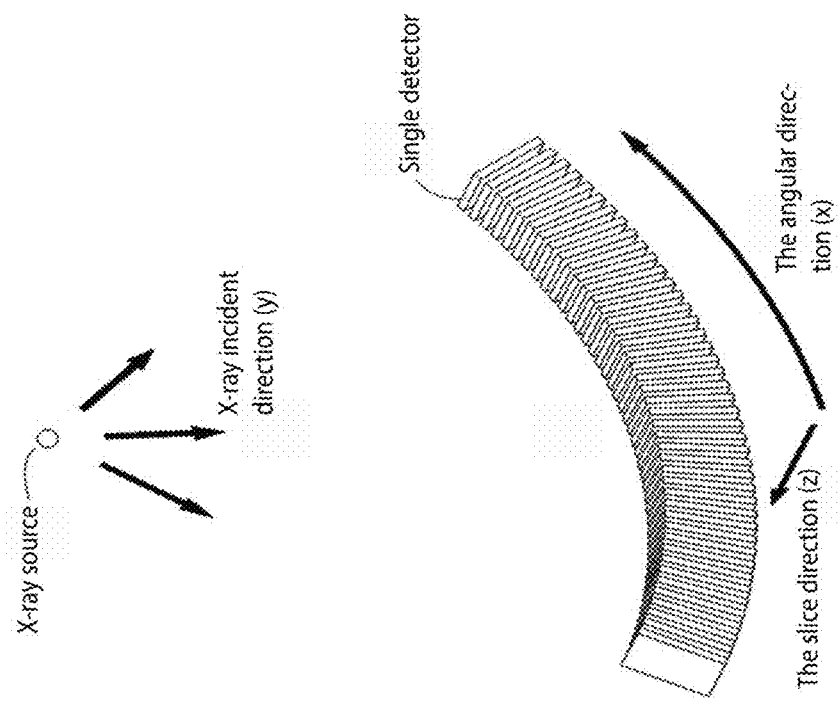
FIG. 4 is a schematic diagram of an x-ray detector according to an exemplary embodiment.
Figure 5:
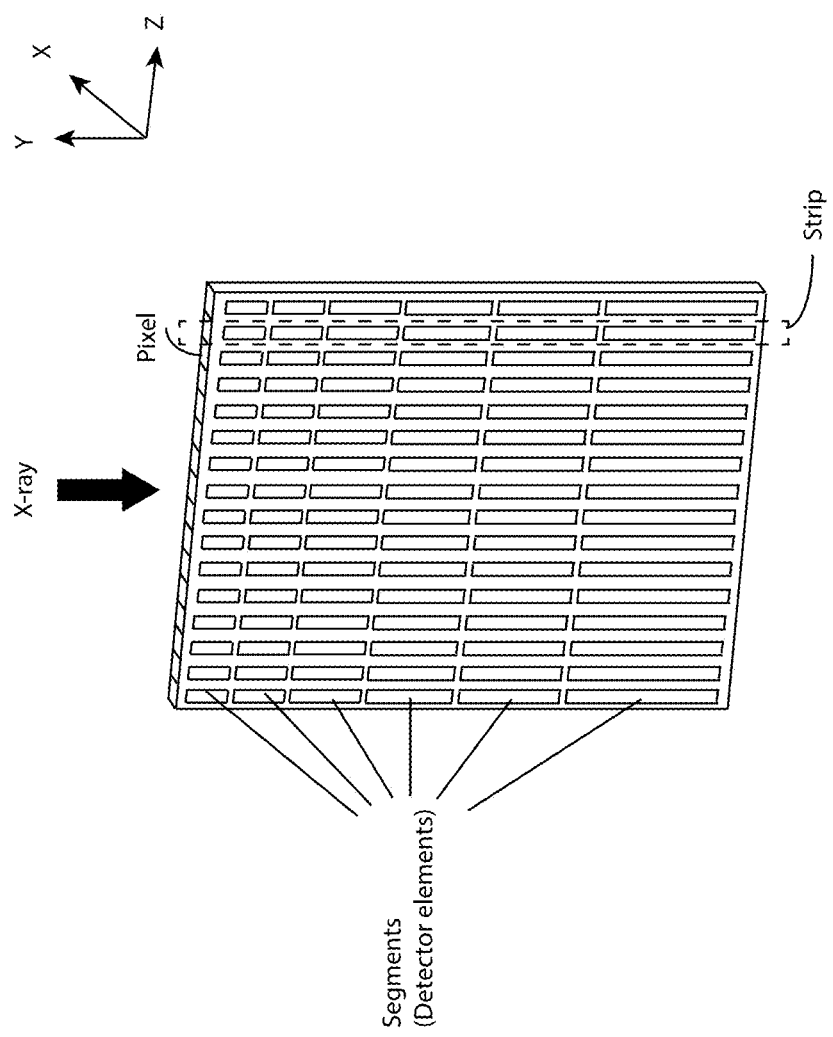
FIG. 5 is a schematic diagram illustrating an example of a semiconductor detector module.
Figure 6:
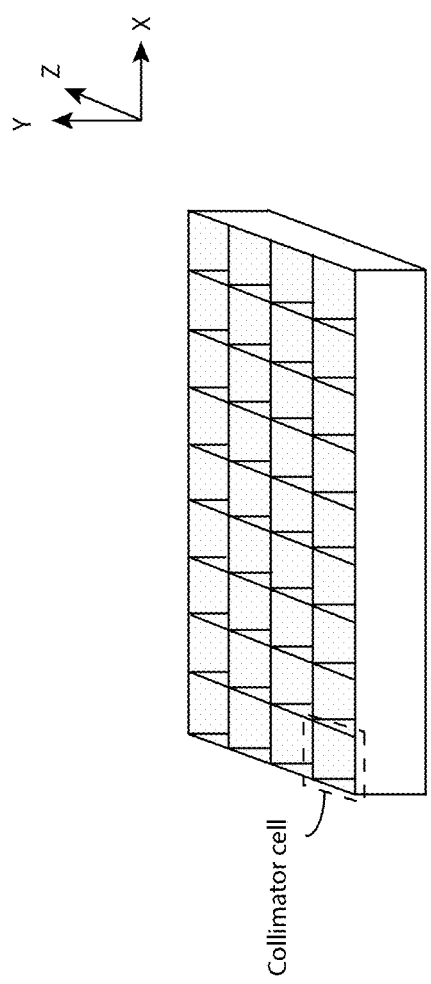
FIG. 6 is a schematic diagram illustrating an example of a two-dimensional object collimator, where a collimator cell is composed of heavy-element lamellas both in the x- and z-directions.
Figure 7:
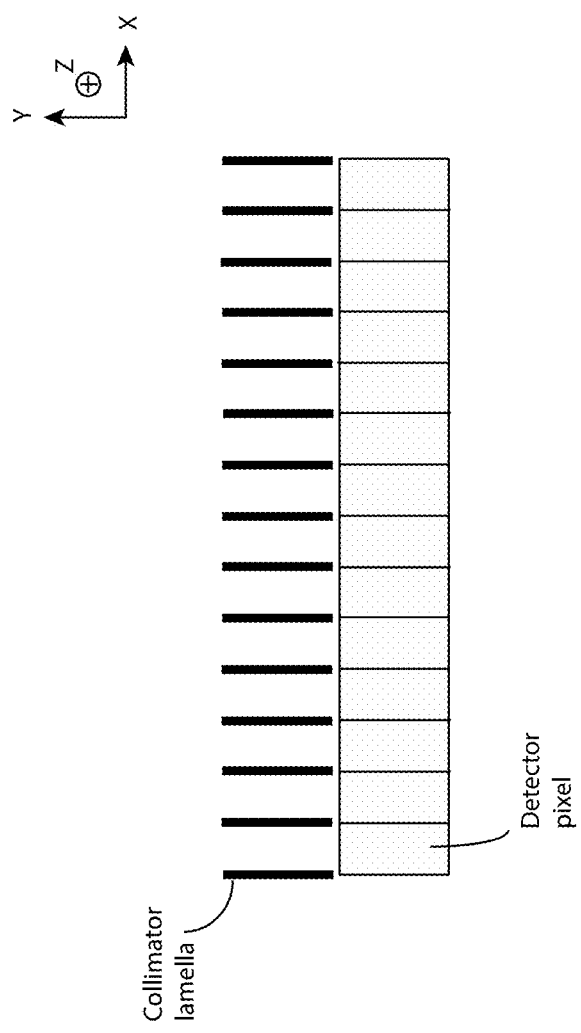
FIG. 7 is a schematic diagram illustrating an example of a view from the z-direction of the cell-to-pixel relationship between a collimator cell and a detector pixel.
Figure 8:
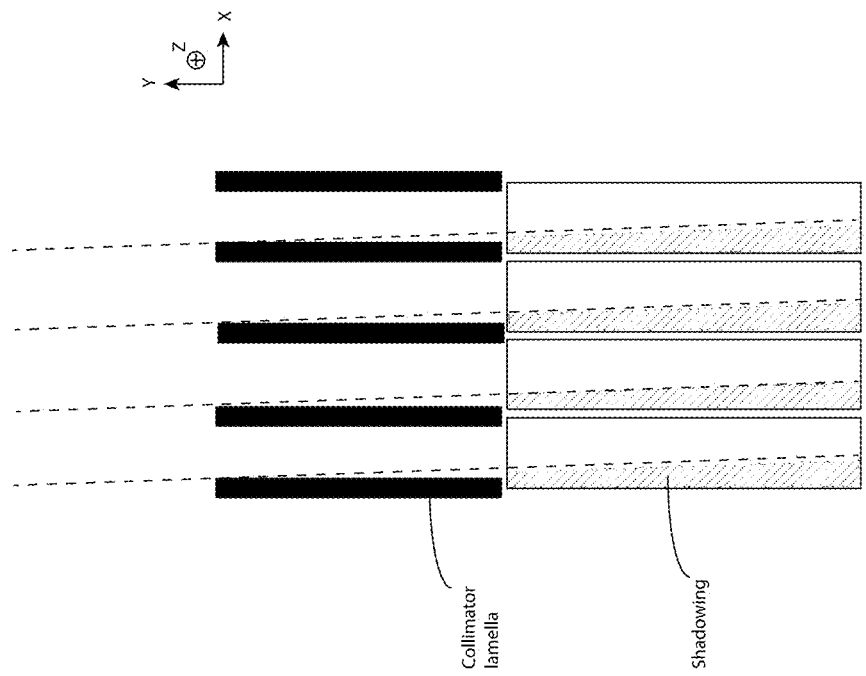
FIG. 8 is a schematic diagram illustrating an example of a misalignment of the x-ray source.
Figure 9:
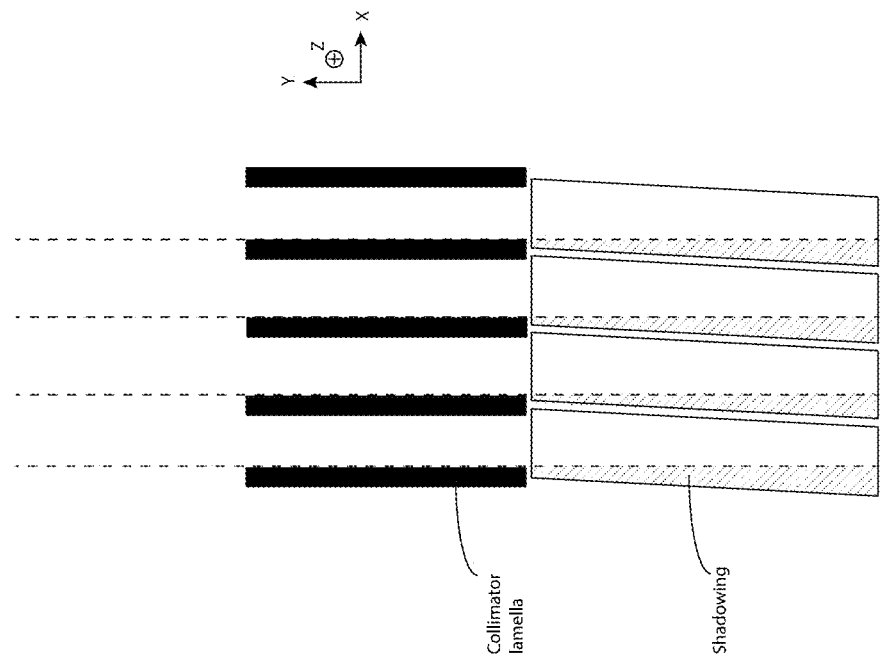
FIG. 9 is a schematic diagram illustrating an example of a misalignment of the detector.
Figure 10:
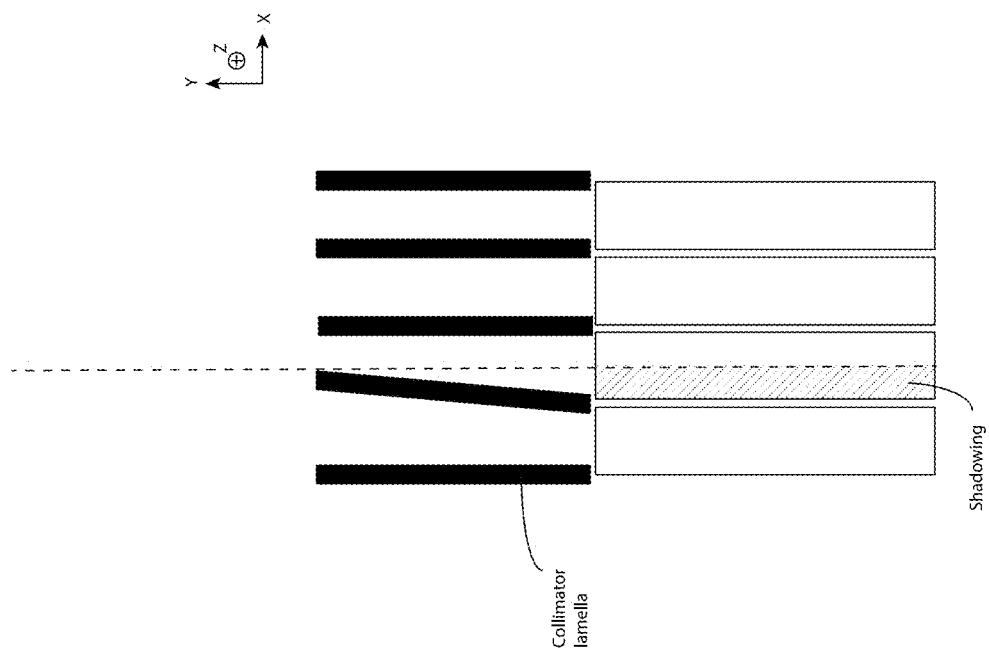
FIG. 10 is a schematic diagram illustrating an example of a misalignment of a collimator lamella.
Figure 11:
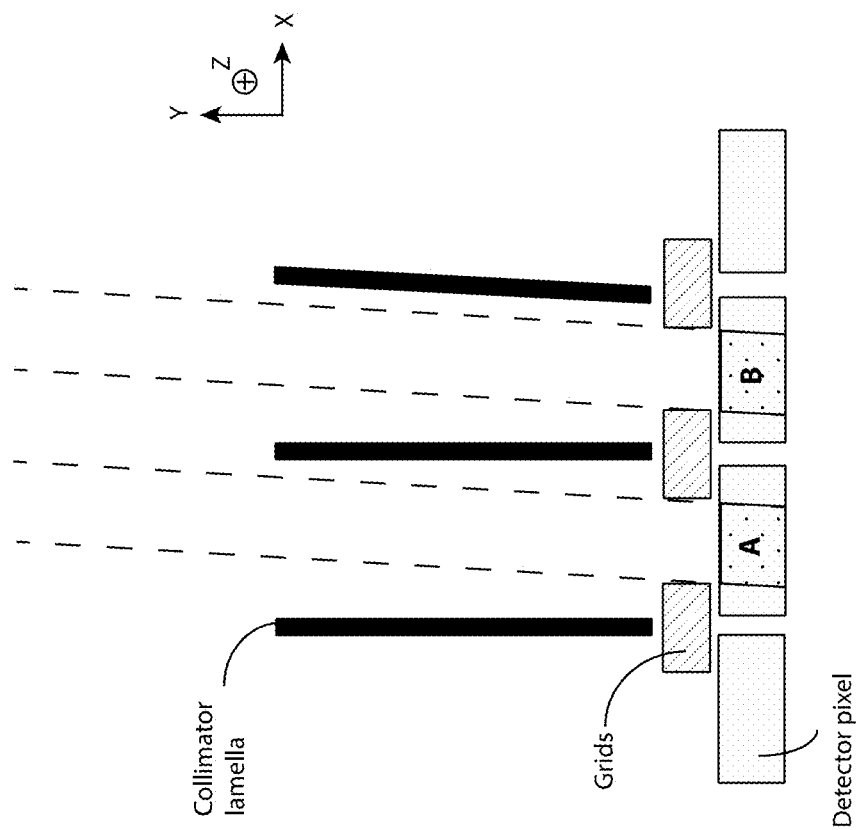
FIG. 11 is a schematic diagram illustrating an example of conventional solution where an extra grid is employed between the object collimator and the detector for avoiding negative effects caused by either dynamic or static misalignments.
Figure 12:
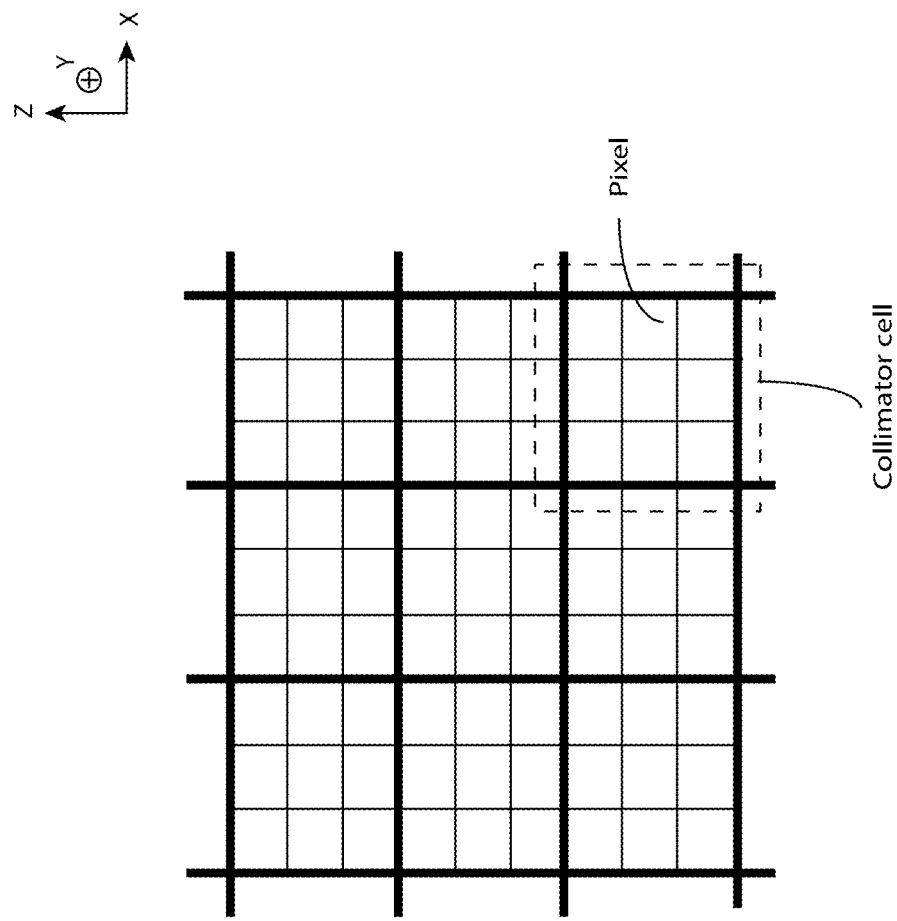
FIG. 12 is a schematic diagram illustrating an example of a view from the y-direction for a proposed geometry between the object collimator and the tiled detector where a collimator cell corresponds to several detector pixels. The geometry is applied on a flat detector.

FIG. 12 is a schematic diagram illustrating an example of a view from the y-direction for a proposed geometry between the object collimator and the tiled detector where a collimator cell corresponds to several detector pixels. The geometry may be applied on a flat detector. FIG. 12 shows an example embodiment of the proposed geometry for which one collimator cell corresponds to nine (3×3) independent detector pixels.

Figure 13:
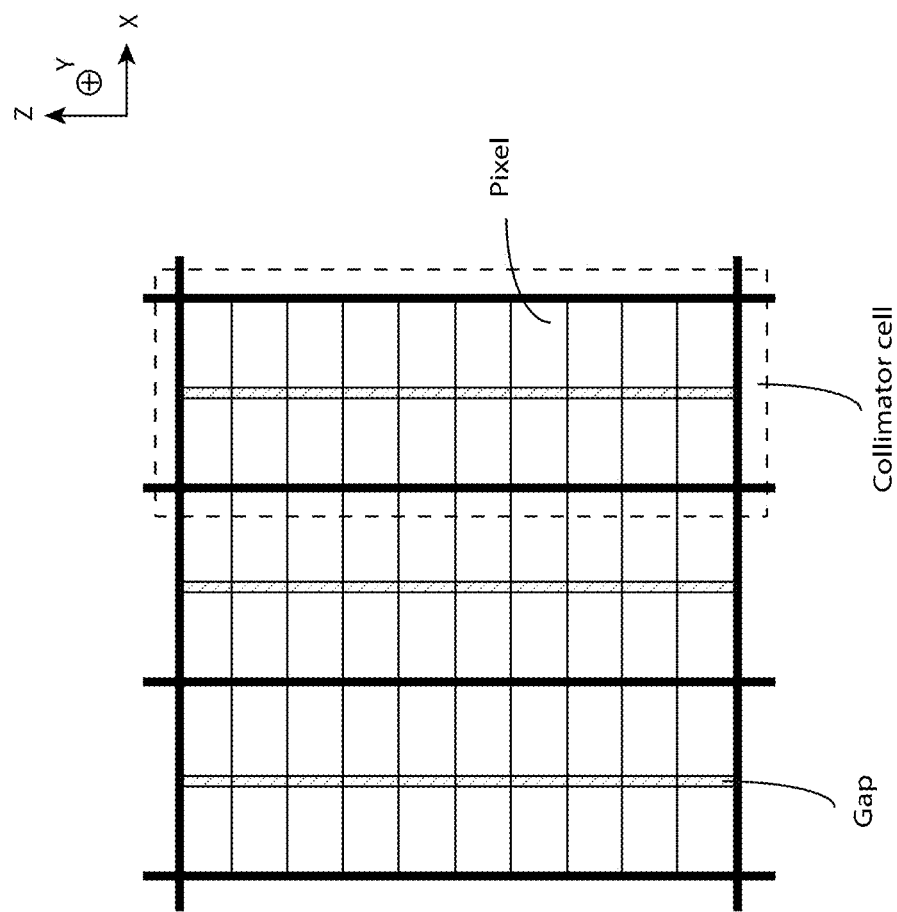
FIG. 13 is a schematic diagram illustrating an example of a view from the y-direction for a proposed geometry between the object collimator and the tiled detector where a collimator cell corresponds to several detector pixels. The geometry is applied on an array of edge-on detectors.

FIG. 13 is a schematic diagram illustrating an example of a view from the y-direction for a proposed geometry between the object collimator and the tiled detector where a collimator cell corresponds to several detector pixels. The geometry may be applied on an array of edge-on detectors. FIG. 13 shows another example embodiment of the proposed geometry for which one collimator cell corresponds to 20 (2×10) independent detector pixels.

For an edge-on x-ray detector having detector modules constructed from semiconductor wafers, there will be one direction on the detector which is along the wafer (z in FIG. 13), and another direction which is orthogonal to the wafer (x in FIG. 13).

In the examples discussed, there is a N×M matrix of pixels matched with each of at least a subset of the collimator cells.

In the following, non-limiting examples of a collimator geometry for edge-on photon-counting detectors for minimizing the effect of shadowing due to misalignment will be described.

By way of example, a collimator structure may be provided where the collimator lamella in the direction along the wafer is an extension of a sheet of attenuating material that lies between detector wafers, where the part of the attenuating material that lies above the detector wafers has a larger thickness than that which lies between the wafers. The benefit from such a structure is that the thicker attenuating material above the wafers block radiation which otherwise could have impinged on the side of the wafer (it is desirable that all radiation passes/enters through the edge of the wafer in order to obtain a uniform detector response). Avoiding x-rays that impinge on the side of the wafers lowers the sensitivity to misalignment. For example, if x-rays impinge on the side of the wafer there will be a higher number of detected x-rays since the un-attenuated x-ray beam impinges directly on the large area of the wafer side, and if the alignment changes such that the side of the wafer is no longer illuminated, there will be a large reduction of the number of detected photons, resulting in a more difficult calibration problem.

Figure 14:
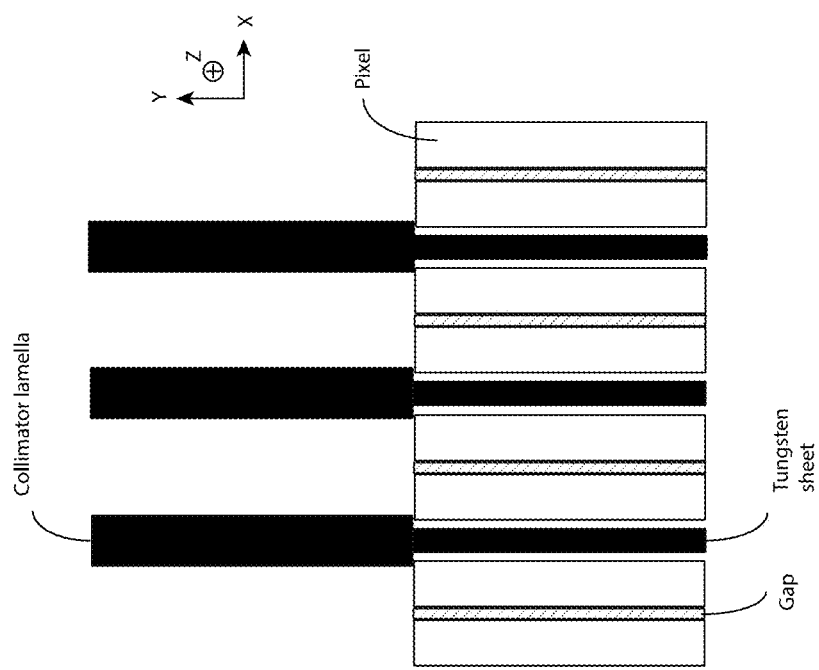
FIG. 14 is a schematic diagram illustrating an example of a view from the z-direction for a proposed geometry between the object collimator and the tiled detector where a collimator cell corresponds to two pixels in one direction.

FIG. 14 is a schematic diagram illustrating an example of a view from the z-direction for a proposed geometry between the object collimator and the tiled detector where a collimator cell corresponds to two detector pixels in one direction (such as that illustrated in FIG. 13).

In other words, there is provided an x-ray detector comprising a plurality of edge-on detector modules arranged side-by-side and adapted to be oriented edge-on towards an x-ray source. The x-ray detector further comprises an x-ray attenuating structure arranged between at least a subset of the edge-on detector modules, and a collimator structure arranged in the x-ray path between the x-ray source and the edge-on detector modules. The collimator structure comprises at least one collimator lamella arranged as an extension of the x-ray attenuating structure and having a larger thickness than the thickness of the x-ray attenuating structure situated between the edge-on detector modules. An example of such a collimator structure is illustrated in FIG. 14.

By way of example, the collimator lamella and the x-ray attenuating structure situated between the edge-on detector modules may be connected, joined or integrated with each other.

For example, the x-ray attenuating structure may comprise at least one x-ray attenuating sheet or anti-scatter foil.

In a particular example, the edge-on detector modules have a charge collecting front-side and a back-side, and at least a subset of the edge-on detector modules are pairwise arranged front-side to front-side, wherein the at least one collimator lamella covers the front-side to front-side "gap" between the front-sides.

Figure 15:
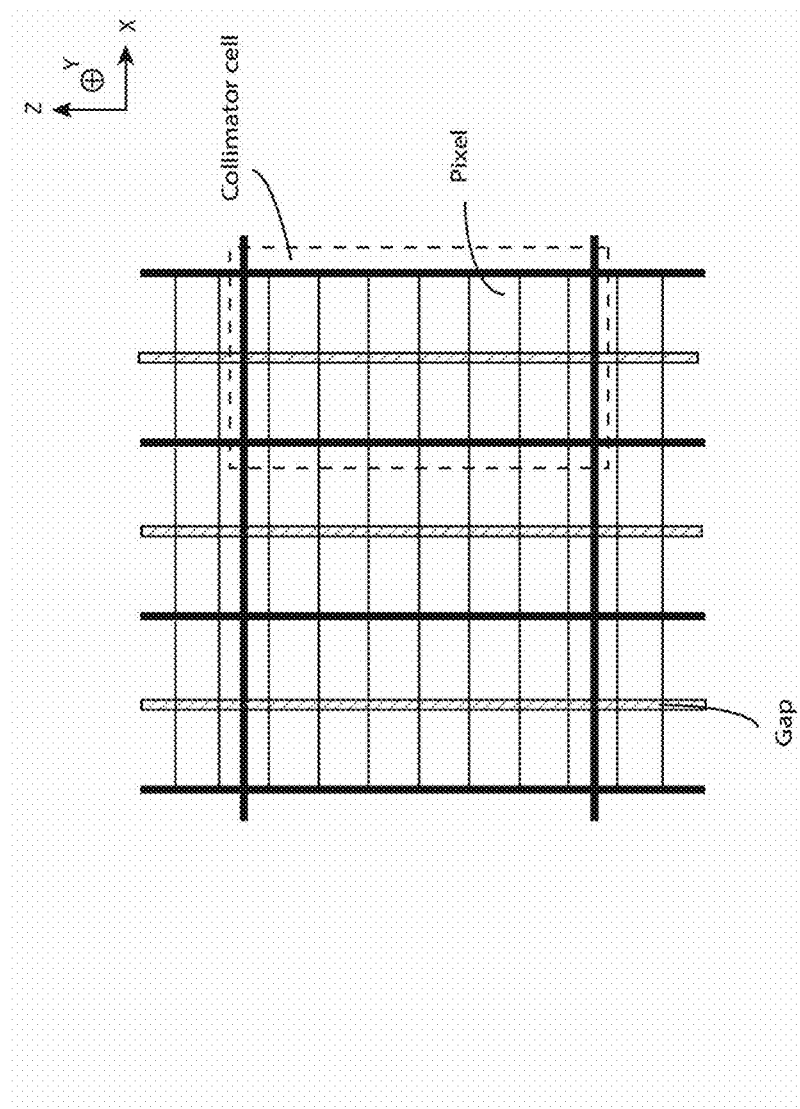
FIG. 15 is a schematic diagram illustrating an example of an x-ray detector with a collimator structure having at least one collimator cell that is offset relative to the pixel boundaries.

FIG. 15 is a schematic diagram illustrating an example of an x-ray detector with a collimator structure having at least one collimator cell that is offset relative to the pixel boundaries.

In this example, the x-ray detector comprises a plurality of edge-on detector modules arranged side-by-side and adapted to be oriented edge-on towards an x-ray source, each edge-on detector having at least one detector pixel. The x-ray detector also comprises a collimator structure arranged in the x-ray path between the x-ray source and the edge-on detector modules. The collimator structure comprises at least one collimator cell corresponding to an N×M matrix of pixels, where at least one of N and M is greater than one, and at least one collimator lamella of the collimator cell is arranged to be offset relative a boundary between pixels.

Normally, the edge-on detector modules have an extension sidewise and lengthwise, and the collimator lamellas of the collimator cell that are orthogonal to the lengthwise extension of the detector modules may for example be arranged to be offset relative pixel boundaries.

In other words, an example of the proposed geometry relates to a collimator structure having collimator cells where the collimator lamellas that are orthogonal to the wafers lie within the detector pixels (not on pixel boundaries). This is beneficial for managing misalignment since the shadow from the collimator lamella will always lie within the same pixel, and not switch from one pixel to another. Also, the spectral distortion due to shadowing will be minimal, since the profile of the shadow is approximately the same width at all depths in the detector material, this, together with the shadow lying entirely within one pixel, implies that a change in the shadowing can only result in a change of the photon flux with a constant factor for all energies. If the collimator lamella was placed on the boundary between pixels, both pixels that are adjacent to the collimator lamella would experience larger photon flux variations and also spectral variations as a consequence of misalignment.

Figure 16:
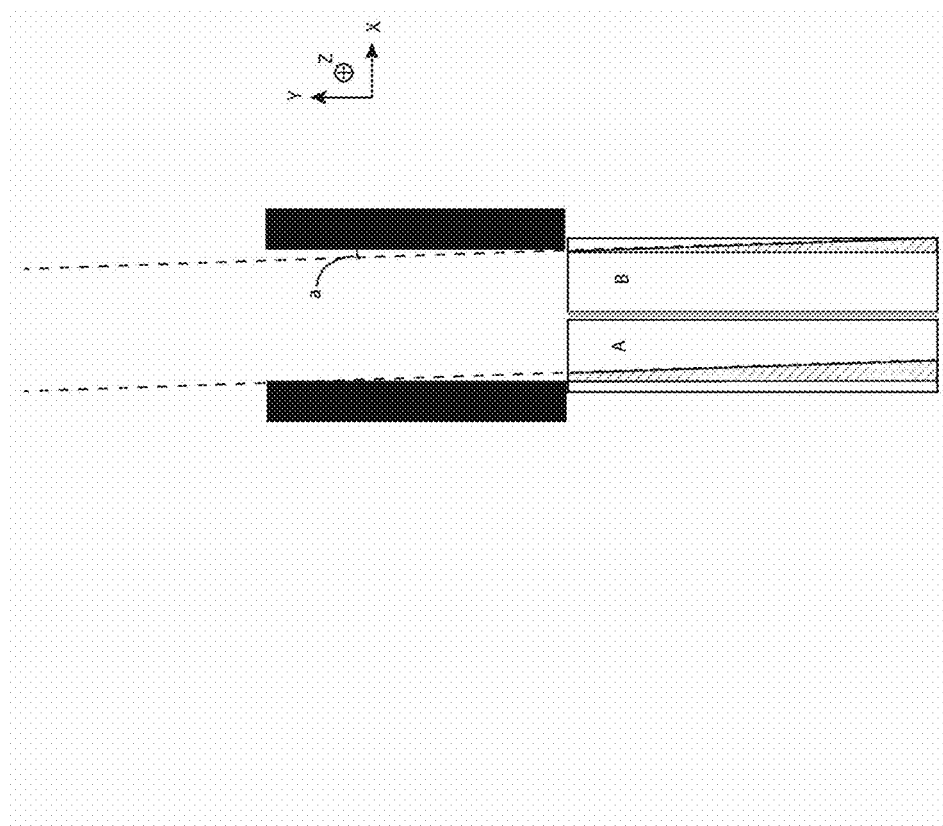
FIG. 16 is a schematic diagram illustrating an example of the symmetry that two pixels within a collimator cell holds in case of x-ray source misalignment.
Figure 17:
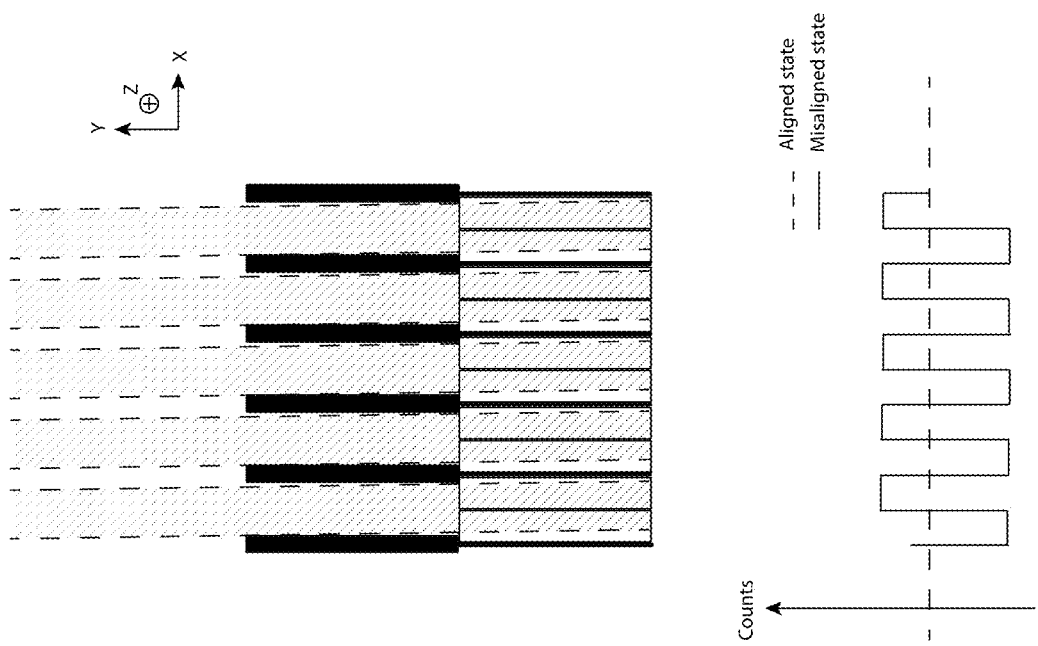
FIG. 17 is a schematic diagram illustrating an example of the periodic signal that can be obtained by the detector in case of a source misalignment under the proposed geometry.

More generally, the pixels located on the different sides of the collimator lamella will be sensitive to misalignments in different directions, i.e. if the source moves some pixels will react by detector less photons and some pixels that will react by detector more photons. This is illustrated in FIG. 16, which shows that a misalignment with respect to the direction of the x-rays with the angle "a" results in less illumination of pixel A and more illumination in the pixel B. FIG. 17 illustrates that the effect can be seen in many pixels at the same time since the geometric misalignment effect the entire detector. The position of the x-ray source can then be estimated by, for example, monitoring the ratio of the counts registered on either side of a collimator lamella. At the aligned position, the number of counts are equal for both pixels (if differences in gain have been calibrated) since they are both fully illuminated, and at a misaligned position, the angular misalignment can be calculated using the height of the collimator and the degree of shadowing. For example, consider a 1 mm wide pixel that has been shadowed by a 30 mm long collimator such that it has lost 5% of its maximum counts. An estimate of the angular misalignment (alpha) can then be calculated using that: tan(alpha)=0.05*10/30. In order to improve the accuracy of this estimation, a calibration scan prior to the image acquisition can be performed in which the source is deliberately moved and the number of counts in each pixel is monitored. The obtained photon counts can then, for example, be stored in a look-up table that can be used to determine the alignment state during the image acquisition.

In other words, for each measurement, or set of measurements, the detected signal from a designated reference set of pixels located outside of the imaged object are monitored and the obtained signal is used for establishing the occurrence of a geometrical misalignment. The requirement on the reference set of pixels is that they contain pixels with different response to shadowing, i.e. a subset of the pixels measure an increase in the number of counts as a consequence of shadowing, and another subset of the pixels measure a decrease in the number of counts as a consequence of shadowing. The different responses are necessary in order to distinguish shadowing from a drift of, for example, the current of the x-ray tube (mA) or the acceleration voltage of the x-ray tube (kVp).

A drift of the x-ray tube current (mA) results in an equal increase in the number of counts for all energy bins and pixels. If a change in shadowing occurs, each pixel and energy bin can experience different changes in the number of registered counts. If all pixels respond to shadowing in the same way (i.e. all increase or all decrease) then shadowing cannot easily be distinguished from for example mA drift since all pixels and energy bins will have a component in the same direction which could be mistaken for a mA drift.

In the disclosed invention, there is no need for dedicated pixels that monitor the misalignment (as is the case when using deliberately misaligned collimator lamellas, or pixel masks). All pixels on the detector can in principle be used to estimate the alignment, if they are located outside of the imaged object at the time for the estimation. It is simple to estimate if a pixel lies outside of the imaged object from the acquired CT sinogram data since the profile of the object is easy to identify.

Once the position of the x-ray tube relative to the detector/collimator has been estimated, the obtained estimate can be used to, for example:

1) correct the measured x-ray counts in pixels located behind the object 2) estimate a set of geometric parameters that can be used as input to the image reconstruction.

Depending on the collimator geometry, it may be desirable to employ a spectral, photon-counting detector. For the geometry presented in FIG. 13, in order to be able to perform 1), i.e. correct the measured signal in pixels behind the object it is desirable that the detector is spectral (and photon counting). For the geometry presented in FIG. 15, this may not be necessary. Pixels that are to be corrected will be referred to as target pixels.

Here, an example of a method of correcting the number of counts in the energy bins of a target pixel (a detector pixel that is located behind the imaged object) is presented. First, two categories of energy bins are identified: mono-chromatic and poly-chromatic. A mono-chromatic energy bin is only sensitive in a narrow energy range. For example, only photons with energy between 50 keV and 60 keV can generate a count in the energy bin. A poly-chromatic energy bin is sensitive in a broad energy range, e.g. photons with energies between 10 keV and 120 keV can generate a count in the energy bin. For photon-counting spectral detectors based on silicon, for example, the highest energy thresholds are essentially mono-chromatic, while the lower energy bins are poly-chromatic due to their sensitivity for Compton scatter events (higher energy photons depositing only part of their energy).

Figure 19:
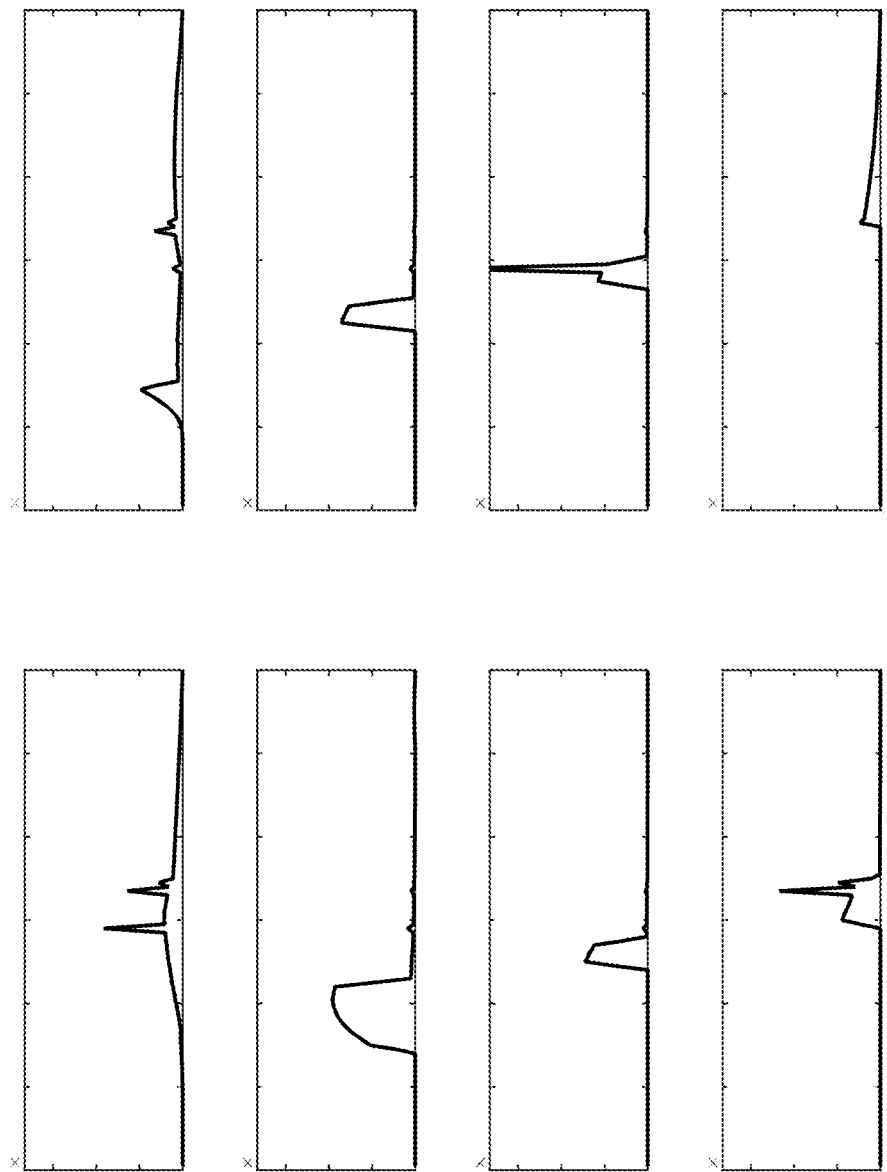
FIG. 19 is an example of the sensitivity of different energy bins of a silicon detector with 8 energy bins, whereof some bins are essentially mono-chromatic and others are poly-chromatic.

FIG. 19 is a schematic diagram illustrating an example of the sensitivity of different energy bins (the energy distribution of the photons that generate a counts in each pixels) for a silicon photon counting detector. In the example of FIG. 19, the energy bins 4 to 8 have very narrow regions of sensitivity and therefore behave as if they were mono-chromatic, i.e. the response to shadowing is independent of the input spectrum. The lower energy bins, on the other hand, have a broad energy response and must be considered to be poly-chromatic.

Figure 20:
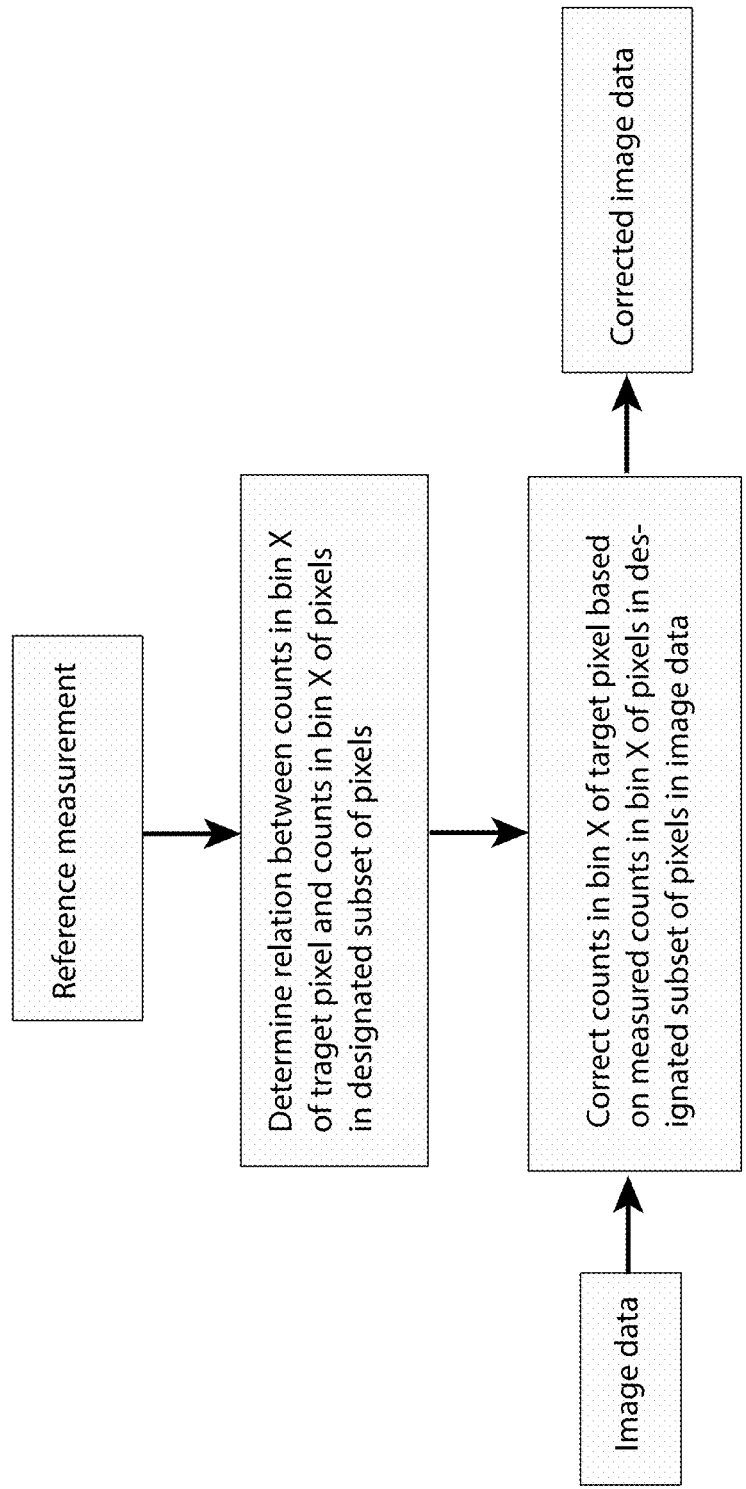
FIG. 20 is a schematic flow diagram showing an example of the steps of calibration of essentially mono-chromatic energy bins.

The correction factors for mono-chromatic energy bins are independent of the input spectrum to the target pixel, which makes them simple to correct. The correction factors can be determined by establishing a direct relationship between the counts in the bin of the target pixel and the corresponding bin of the pixels in the designated reference set. The relationship between the counts in the target pixel and the designated subset of pixels can be established by, for example, performing a set of reference measurements during which typical misalignments occur. Typical misalignments can be obtained either by natural movement of the detector/source system, or by deliberate movement of the focal spot and/or the detector. A flow diagram for performing the calibration of mono-chromatic energy bins is shown in FIG. 20.

Correction factors for poly-chromatic energy bins are largely dependent on the input spectrum to the target pixel and different approach has to be taken in order to compute the correction factors for poly-chromatic energy bins. The following is an example of a step-by-step method for performing a first order correction of the registered counts in poly-chromatic energy bins for which knowledge about input spectrum is required for performing the correction:

1) Estimate the current degree of shadowing from the reference pixels.
2) Use material basis decomposition to estimate the thicknesses of the basis materials in path of the x-ray beam that hits the target pixel. (This estimate will have a slight bias which it is the aim to remove).

3) Use the estimated basis material thicknesses together with a detector response model to estimate the input spectrum to the pixel (also here there will be a bias).
4) Use the estimated degree of shadowing (alpha) together with the estimated input spectrum to compute correction factors for the registered number of counts in the lower energy bins of the target pixel using a detector forward model.
5) Re-do the material basis decomposition using the corrected counts An alternative way of calculating the correction factors is to use a look-up table that directly relates correction factors to basis material thicknesses. In this case, it is not necessary to perform the intermediate step of estimating the input spectrum each time correction factors are to be estimated. Each entry in the look-up table would then contain the correction factors for all energy bins for a particular set of basis material thicknesses.

It is possible to perform the correction iteratively since the estimations of the basis material thicknesses performed using the corrected counts can be used to estimate a new set of correction factors. The new correction factors would be more accurate than the first since the estimation of the basis material thicknesses would be more accurate. The process can be repeated until convergence.

It will be appreciated that the methods and devices described herein can be combined and re-arranged in a variety of ways.

For example, specific functions may be implemented in hardware, or in software for execution by suitable processing circuitry, or a combination thereof.

The steps, functions, procedures, modules and/or blocks described herein may be implemented in hardware using any conventional technology, such as semiconductor technology, discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs). Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

According to an aspect, there is provided a system configured for management of geometric misalignment in an x-ray imaging system having an x-ray source, a photon-counting x-ray detector and an intermediate collimator structure in the x-ray path between the x-ray source and the x-ray detector.

The x-ray detector comprises a plurality of pixels, and the collimator structure comprises a plurality of collimator cells, wherein each of at least a subset of the collimator cells corresponds to a N×M matrix of pixels, where at least one of N and M is greater than one. For example, N≥2 and M≥2.

The system is configured to monitor, for a designated subset of pixels including at least two pixels that are affected differently by shadowing from the collimator structure due to geometric misalignment, output signals from the pixels of the designated subset of pixels. The system is further configured to determine the occurrence of geometric misalignment based on the monitored output signals from the pixels of the designated subset of pixels.

By way of example, the at least two pixels have different responses to the shadowing, and the system is configured to monitor the different responses by measuring the output signals.

For example, the system may be configured to estimate at least one parameter representing the geometric misalignment and/or correct for the geometric misalignment based on the monitored output signals from the pixels of the designated subset of pixels and/or iii) perform post-processing of the output signals and/or iv) image reconstruction based on the parameter(s) representing the geometric misalignment and/or based on the monitored output signals from the pixels of the designated subset of pixels.

According to another aspect, there is also provided an x-ray imaging system comprising the system for management of geometric misalignment as described herein.

Figure 21:
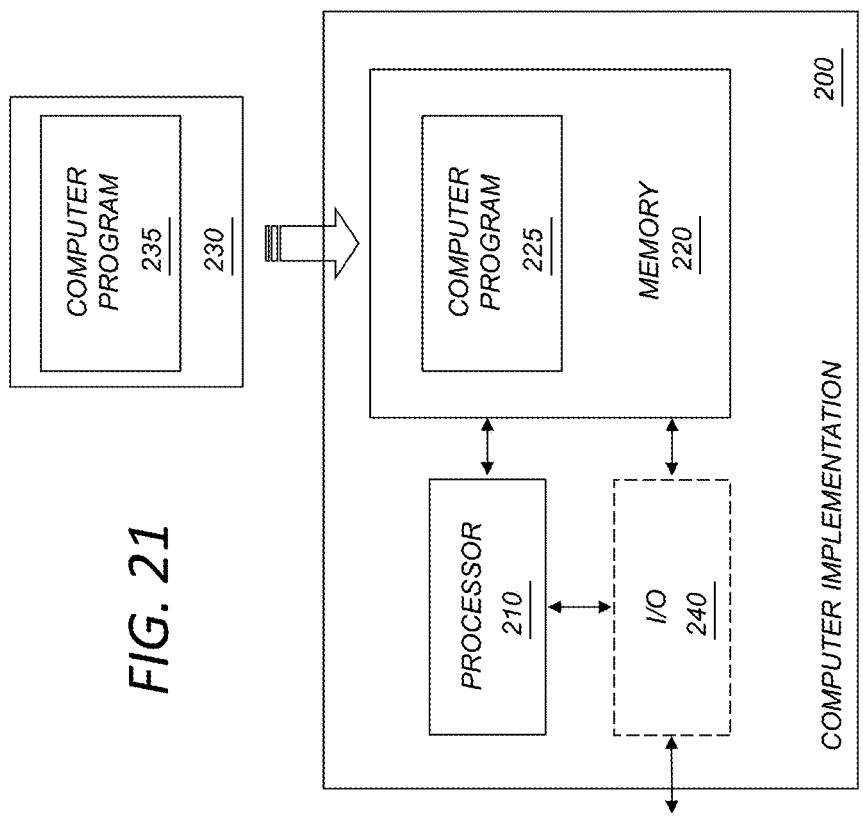
FIG. 21 is a schematic diagram illustrating an example of a computer implementation according to an embodiment.

FIG. 21 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

By way of example, there is provided a computer-program product comprising a computer-readable medium having stored thereon a computer program for management, when executed by a processor, of geometric misalignment in an x-ray imaging system having an x-ray source, a photon-counting x-ray detector and an intermediate collimator structure in the x-ray path between the x-ray source and the x-ray detector. The x-ray detector comprises a plurality of pixels, and the collimator structure comprises a plurality of collimator cells, wherein each of at least a subset of the collimator cells corresponds to a N×M matrix of pixels, where at least one of N and M is greater than one. For example, $N \geq 2$ and $M \geq 2$.

The computer program comprises instructions, which when executed by the processor, cause the processor to:
monitor, for a designated subset of pixels including at least two pixels that are affected differently by shadowing from the collimator structure due to geometric misalignment, output signals from the pixels of the designated subset of pixels; and
determine the occurrence of geometric misalignment based on the monitored output signals from the pixels of the designated subset of pixels.

The method flows presented herein may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively it is possibly to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

The invention claimed is:

1. A method for management of geometric misalignment in an x-ray imaging system having an x-ray source, a photon-counting x-ray detector and an intermediate collimator structure in an x-ray path between the x-ray source and the x-ray detector,
wherein the x-ray detector comprises a plurality of pixels, and the collimator structure comprises a plurality of collimator cells, wherein each of at least a subset of the collimator cells corresponds to an N×M matrix of pixels, where at least one of N and M is greater than one, wherein the method comprises:
monitoring, for a designated subset of pixels including at least two pixels that are affected differently by shadowing from the collimator structure due to geometric misalignment, output signals from the pixels of the designated subset of pixels; and
determining the occurrence of geometric misalignment based on the monitored output signals from the pixels of the designated subset of pixels.

2. The method of claim 1, wherein said at least two pixels have different responses to the shadowing, and the different responses are monitored by measuring the output signals.

3. The method of claim 1, wherein the method further comprises i) estimating at least one parameter representing the geometric misalignment and/or ii) correcting for the geometric misalignment based on the monitored output signals from the pixels of the designated subset of pixels and/or iii) performing post-processing of the output signals and/or iv) image reconstruction based on the parameter(s) representing the geometric misalignment and/or based on the monitored output signals from the pixels of the designated subset of pixels.

4. The method of claim 1, wherein the effect of the geometric misalignment on the output signal(s), or on value(s) based on the output signal(s), of at least one pixel is corrected for based on the monitored output signals from the pixels of the designated subset of pixels.

5. The method of claim 4, wherein said at least one pixel is located behind the object/subject to be imaged during image acquisition.

6. The method of claim 1, wherein the output signals from the pixels represent photon counts of the pixels.

7. The method of claim 1, wherein the output signals from the pixels of the designated subset of pixels are measured during image acquisition of an object/subject and located outside of the object/subject to be imaged during measurement.

8. The method of claim 1, wherein said at least two pixels that are affected differently by shadowing are located with respect to the collimator structure such that they experience different shadowing from the collimator structure due to geometric misalignment.

9. The method of claim 1, wherein said at least two pixels that are affected differently by shadowing include a first subset of one or more pixels having an increase in the number of photon counts as a consequence of the shadowing and a second subset of one or more pixels having a decrease in the number of photon counts as a consequence of the shadowing.

10. The method of claim 1, wherein each of the collimator cells has a first side and a second opposite side, and at least one of the pixels of the designated subset is located on the first side of a collimator cell and at least one of the pixels of the designated subset is located on the second opposite side of the same or another collimator cell.

11. The method of claim 10, wherein the x-ray detector comprises a number of detector modules, and the pixels located on opposite sides of a collimator cell belong to different detector modules of the x-ray detector.

12. The method of claim 1, wherein the geometric misalignment includes a relative geometric misalignment between the x-ray source and the x-ray detector.

13. The method of claim 1, wherein the direction and/or degree of pixel shadowing caused by the geometric misalignment is/are determined based on the monitored output signals from the pixels of the designated subset of pixels.

14. The method of claim 1, wherein the x-ray detector is a photon-counting and energy-discriminating x-ray detector, and the effect of the geometric misalignment on the photon count(s) of said at least one pixel is corrected for based on the monitored output signals, or on value(s) based on the output signal(s), of the pixels of the designated subset of pixels and the associated photon energy information obtained from the photon-counting and energy-discriminating x-ray detector.

15. The method of claim 14, wherein the photon-counting and energy-discriminating x-ray detector is configured to classify the detected photons into energy bins, and the step of correcting for the effect of the geometric misalignment on the photon count(s) comprises applying correction to the photon count(s) in the energy bins of the said at least one pixel based on the monitored photon counts of the pixels of the designated subset of pixels and the associated photon energy information.

16. The method of claim 15, wherein correction factors are determined based on at least one parameter representing the geometric misalignment and basis material thickness.

17. The method of claim 16, wherein the correction factors are determined and applied for the photon counts in lower energy bins.

18. The method of claim 1, wherein a geometric misalignment is distinguished from a drop in current-to-peak-kilovoltage ratio (mA/kVp) of the x-ray source based on the monitored output signals of the pixels of the designated subset of pixels.

19. The method of claim 1, wherein the management of geometric misalignment includes supervision and/or handling of the geometric misalignment such as monitoring and/or correcting/calibrating for the geometric misalignment.

20. A system configured for management of geometric misalignment in an x-ray imaging system having an x-ray source, a photon-counting x-ray detector and an intermediate collimator structure an x-ray path between the x-ray source and the x-ray detector,
wherein the x-ray detector comprises a plurality of pixels, and the collimator structure comprises a plurality of collimator cells, wherein each of at least a subset of the collimator cells corresponds to an N×M matrix of pixels, where at least one of N and M is greater than one,
wherein the system is configured to monitor, for a designated subset of pixels including at least two pixels that are affected differently by shadowing from the collimator structure due to geometric misalignment, output signals from the pixels of the designated subset of pixels; and
wherein the system is configured to determine the occurrence of geometric misalignment based on the monitored output signals from the pixels of the designated subset of pixels.

21. The system of claim 20, wherein said at least two pixels have different responses to the shadowing, and the system is configured to monitor the different responses by measuring the output signals.

22. The system of claim 20, wherein the system is further configured to estimate at least one parameter representing the geometric misalignment and/or correct for the geometric misalignment based on the monitored output signals from the pixels of the designated subset of pixels and/or iii) perform post-processing of the output signals and/or iv) image reconstruction based on the parameter(s) representing the geometric misalignment and/or based on the monitored output signals from the pixels of the designated subset of pixels.

23. An x-ray imaging system comprising the system of claim 20.

24. A computer-program product comprising a computer-readable medium having stored thereon a computer program for management, when executed by a processor, of geometric misalignment in an x-ray imaging system having an x-ray source, a photon-counting x-ray detector and an intermediate collimator structure in an x-ray path between the x-ray source and the x-ray detector, wherein the x-ray detector comprises a plurality of pixels, and the collimator structure comprises a plurality of collimator cells, wherein each of at least a subset of the collimator cells corresponds to an N×M matrix of pixels, where at least one of N and M is greater than one,
wherein the computer program comprises instructions, which when executed by the processor, cause the processor to:
monitor, for a designated subset of pixels including at least two pixels that are affected differently by shadowing from the collimator structure due to geometric misalignment, output signals from the pixels of the designated subset of pixels; and
determine the occurrence of geometric misalignment based on the monitored output signals from the pixels of the designated subset of pixels.

* * * * *